(12) United States Patent
Kaisermayer

(10) Patent No.: US 11,008,542 B2
(45) Date of Patent: May 18, 2021

(54) ASEPTICALLY CONNECTABLE SENSOR PATCH

(71) Applicant: Cytiva Sweden AB, Uppsala (SE)

(72) Inventor: Christian Kaisermayer, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 94 days.

(21) Appl. No.: 15/545,378

(22) PCT Filed: Jan. 29, 2016

(86) PCT No.: PCT/EP2016/051954
§ 371 (c)(1),
(2) Date: Jul. 21, 2017

(87) PCT Pub. No.: WO2016/124500
PCT Pub. Date: Aug. 11, 2016

(65) Prior Publication Data
US 2018/0002653 A1  Jan. 4, 2018

(30) Foreign Application Priority Data

Feb. 4, 2015 (SE) .................................... 1550111-7

(51) Int. Cl.
| | |
|---|---|
| *C12M 1/00* | (2006.01) |
| *C12M 1/34* | (2006.01) |
| *A61M 39/10* | (2006.01) |
| *A61M 39/18* | (2006.01) |
| *C12M 1/12* | (2006.01) |
| *C12M 3/00* | (2006.01) |

(52) U.S. Cl.
CPC ............ *C12M 37/04* (2013.01); *C12M 23/00* (2013.01); *C12M 23/14* (2013.01); *C12M 23/26* (2013.01); *C12M 23/28* (2013.01); *C12M 23/46* (2013.01); *C12M 41/00* (2013.01)

(58) Field of Classification Search
CPC ....... C12M 37/04; C12M 23/14; C12M 23/26
USPC .......................................................... 422/73
See application file for complete search history.

(56) References Cited

U.S. PATENT DOCUMENTS

| | | | |
|---|---|---|---|
| 2005/0163667 A1 | 7/2005 | Krause | |
| 2005/0239197 A1 | 10/2005 | Katerkamp et al. | |
| 2007/0185472 A1 | 8/2007 | Baumfalk et al. | |
| 2011/0124035 A1* | 5/2011 | Broadley | ............... C12M 41/00 435/29 |

(Continued)

FOREIGN PATENT DOCUMENTS

| | | |
|---|---|---|
| DE | 102004015703 A1 | 11/2005 |
| WO | 2010/017519 A1 | 2/2010 |

(Continued)

OTHER PUBLICATIONS

PCT International Search Report and Written Opinion for PCT Application No. PCT/EP2016/051954 dated Apr. 11, 2016 (11 pages).

(Continued)

*Primary Examiner* — Holly Kipouros
(74) *Attorney, Agent, or Firm* — Eversheds Sutherland (US) LLP

(57) ABSTRACT

The invention discloses a first connection unit having a plurality of sensor surfaces and which is adapted to be aseptically connected to a second connection unit mounted e.g. on a flexible bioreactor bag.

19 Claims, 4 Drawing Sheets

(56) References Cited

U.S. PATENT DOCUMENTS

| | | | |
|---|---|---|---|
| 2011/0236962 A1 | 9/2011 | Loebbert et al. | |
| 2013/0289517 A1* | 10/2013 | Williams | F16L 37/098 |
| | | | 604/500 |
| 2014/0170671 A1* | 6/2014 | McGarr | B01L 3/5025 |
| | | | 435/7.1 |
| 2014/0260712 A1* | 9/2014 | Damren | G01D 11/24 |
| | | | 73/866.5 |
| 2015/0344161 A1* | 12/2015 | Selker | B65B 55/02 |
| | | | 422/534 |

FOREIGN PATENT DOCUMENTS

| | | | | |
|---|---|---|---|---|
| WO | 2011/075036 A1 | 6/2011 | | |
| WO | 2012/128703 A1 | 9/2012 | | |
| WO | WO-2013063550 A1 * | 5/2013 | ............ | A61M 39/18 |
| WO | 2013/147688 A1 | 10/2013 | | |
| WO | 2015/184189 A1 | 12/2015 | | |

OTHER PUBLICATIONS

PCT International-Type Search Report for ITS/SE15/00016 dated Feb. 4, 2015 (6 pages).

Weichert et al., "Integrated Optical Single-Use Sensors: Moving Toward a True Single-Use Factory for Biologics and Vaccine Production," BioProcess International, 2014, 12(5), http://www.bioprocessintl.com/upstream-processing/upstream-single-use-technologies/integrated-optical-single-use-sensors-moving-toward-true-single-use-factory-biologics-vaccine-production/.

Database WPI, XP-002755786 (1 page).

Japanese Office Action for JP Application No. 2017-539615 dated Feb. 10, 2020 (9 pages with English translation).

\* cited by examiner

ASEPTICALLY CONNECTABLE SENSOR PATCH

CROSS REFERENCE TO RELATED APPLICATIONS

This application claims the priority benefit of PCT/EP2016/051954 filed on Jan. 29, 2016 which claims priority benefit of Swedish Application No. 1550111-7 filed Feb. 4, 2015. The entire contents of which are hereby incorporated by reference herein.

TECHNICAL FIELD OF THE INVENTION

The present invention relates to aseptic connectors, and more particularly to aseptic connectors with sensors useful in the cultivation of cells. The invention also relates to a method of forming an aseptic connection.

BACKGROUND OF THE INVENTION

In the production of biopharmaceuticals there is a trend towards single-use systems, not least for the cell cultivation operations. Typical single-use systems for cell cultivation involve bioreactors where the cell culture is contained in a flexible bag, either an inflatable self-supporting bag where agitation is provided by rocking (see e.g. U.S. Pat. No. 6,190,913), or a bag supported by a stainless steel support structure where agitation is usually provided by an impeller (see e.g. U.S. Pat. No. 7,629,167) or pneumatically (see e.g. WO 2007/068945A1).

In both types of system there is a need for applying sensors in contact with the cell culture, in order to monitor important variables such as cell density, pH, oxygen concentration and concentrations of various metabolites and/or nutrients. Such sensors are typically integrated with the bag via welded ports as in EP2503320. However, many sensors cannot be sterilised by the same methods that are preferred to use for sterilisation of the bag.

Accordingly there is a need for a convenient technology to connect separately packaged sensors aseptically to a single-use bioreactor bag.

SUMMARY OF THE INVENTION

One aspect of the invention is to provide a connection unit for aseptic connection of sensors to a bioreactor bag. This is achieved with a first connection unit as defined in claim 1.

One advantage is that the connection unit can be packaged separately and be sterilized by a different method than the bioreactor bag. Further advantages are that the sensors can be stored under refrigeration and that the risk of damage to the sensors by folding of the bag can be eliminated. Yet further advantages are that the number of ports on the bag can be minimized and that several different sensor combinations can conveniently be provided for one single bag type.

A second aspect of the invention is to provide a connection unit to be mounted on a bag and capable of connecting aseptically to a connection unit with sensors. This is achieved with a second connection unit as defined in the claims.

A third aspect of the invention is to provide an aseptic connection of sensors to a bioreactor bag. This is achieved with a connection as defined in the claims.

A fourth aspect of the invention is to provide a method of aseptically connecting sensors to a bioreactor bag. This is achieved with a method as defined in the claims.

Further suitable embodiments of the invention are described in the dependent claims.

DRAWINGS

DETAILED DESCRIPTION OF EMBODIMENTS

Figure 1:
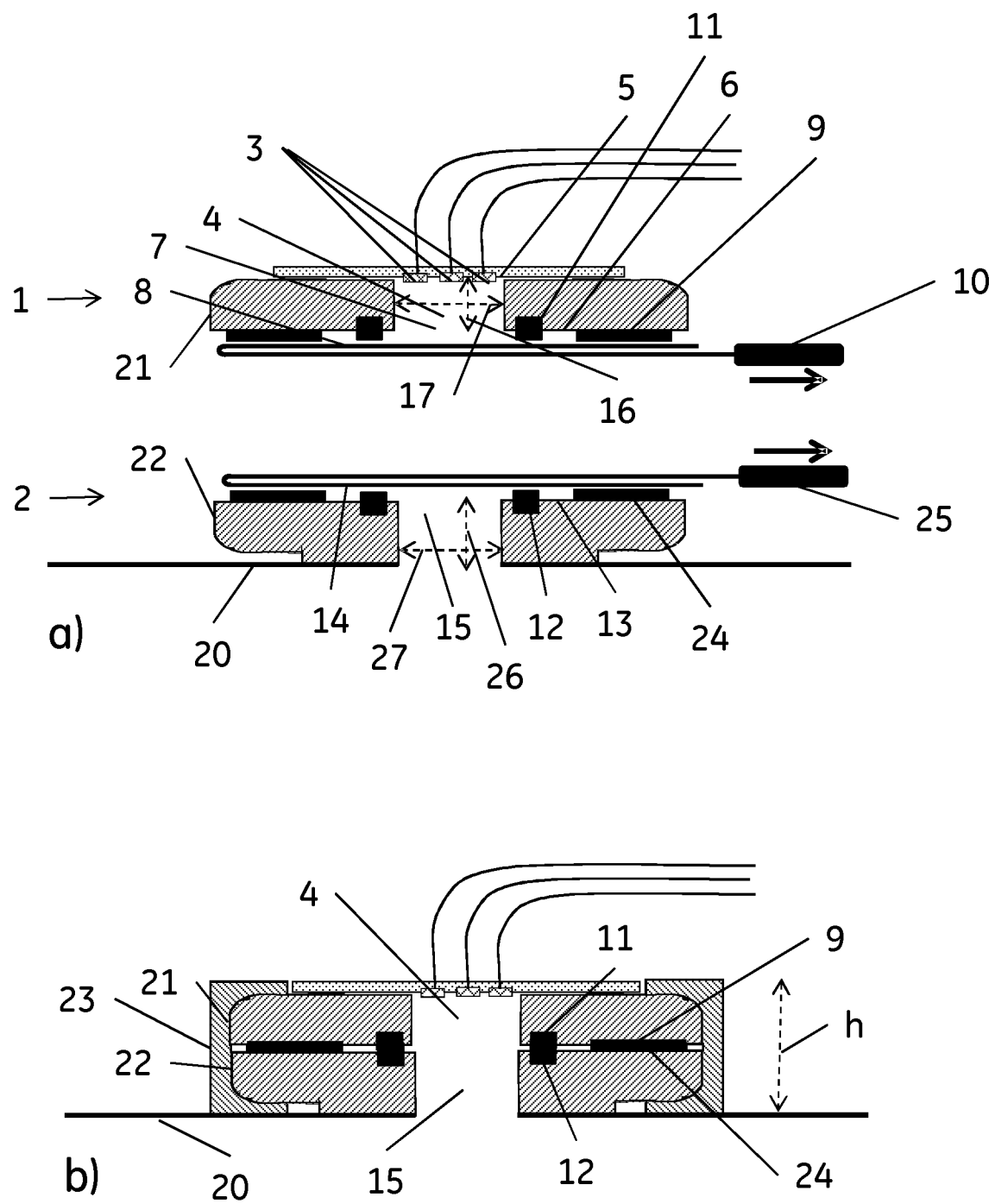
FIG. 1 shows a first and a second connection unit of the invention, a) before connection and b) after connection and clamping.
Figure 2:
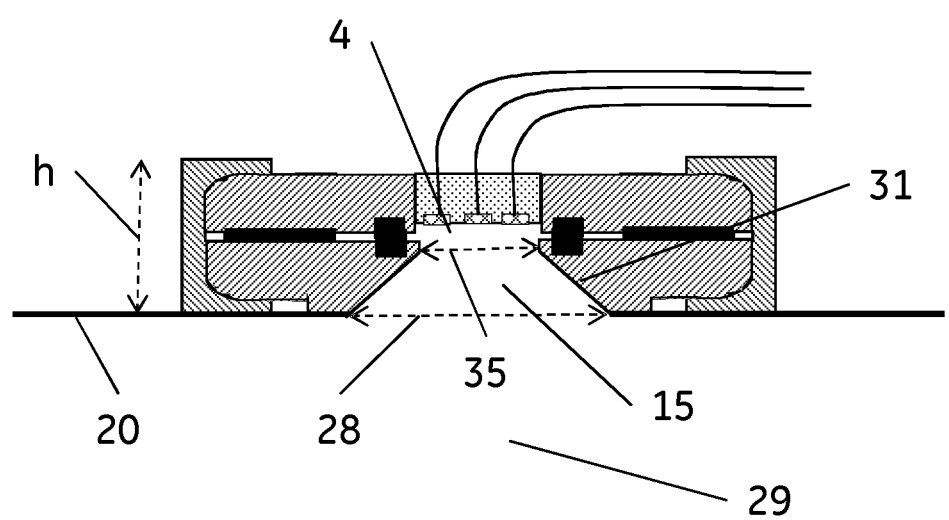
FIG. 2 shows a first and a second connection unit of the invention after connection and clamping.
Figure 3:
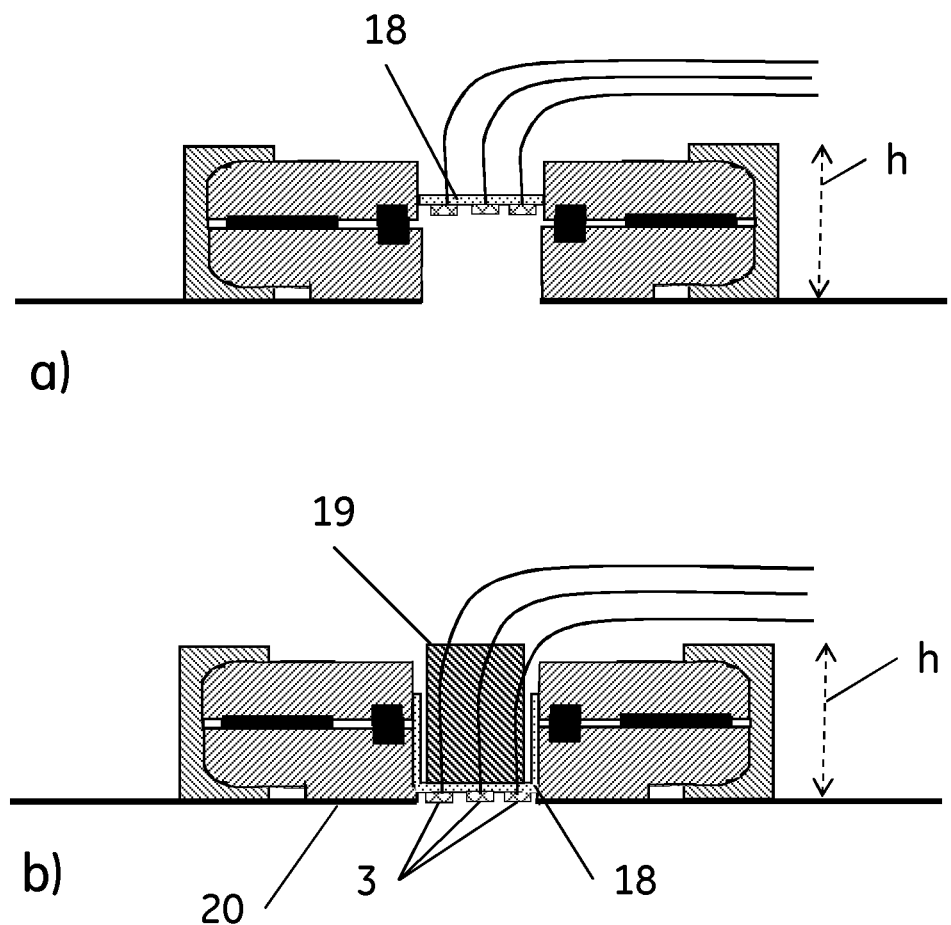
FIG. 3 shows a first and a second connection unit of the invention, a) after connection and clamping and b) after movement of the sensors towards the bag wall.

In one aspect, illustrated by FIGS. 1-3, the present invention discloses a first connection unit 1, which is adapted to mate aseptically with a second connection unit 2, wherein the first connection unit comprises a plurality of sensor surfaces 3. The sensors can suitably be located in a recess 4, or on an inner surface 5 of the recess, which recess is sealed from the ambient environment before mating and which after mating is fluidically connected to the interior 29 of a bioreactor bag 30 via the second connection unit. The first connection unit may comprise a first terminal end surface 6, which is provided with a first opening 7 of the recess 4, wherein the opening is sealed by at least a first releasably adherent film 8. This film can be arranged on the first connection unit, such that the contact between the film and the first connection unit and/or the recess is aseptic. The film can e.g. be held in place by an adhesive foam donut 9, applied on the terminal end of the unit outside the opening 7. The film can also suitably be folded over 180 degrees and, if desired, fitted with a tab 10 to facilitate removal. Further, the first unit may have a gasket 11 mounted on the first terminal surface, adapted to be in sealing abutment with a similar gasket 12 mounted on a second terminal surface 13 of the second connection unit 2. The first releasably adherent film 8 can be arranged to mate with a second releasably adherent film 14 arranged on the second terminal surface 13 of the second connection unit, having a second opening 15, and the first and second films can be adapted to be pulled out together two and two after mating, such that corresponding first 7 and second 15 openings in the first and second terminal end surfaces are mated aseptically. The first and second connector units can suitably have circular cross sections. They can further both comprise a flange 21, 22 adapted to engage with a clamp 23 to secure the connection after mating. The flanges can e.g. be adapted to engage with the well-known Tri-Clamp™ or Tri-Clover™ clamps, which are also disclosed in the ISO 2852 standard.

In certain embodiments, the first connector unit comprises at least two, such as at least three or at least four sensor surfaces. It is advantageous to have several sensor surfaces in the same connector unit, in that only one port is needed. Cultivation of cells typically requires the monitoring of several variables and it is desirable to have a minimum number of ports, as each port adds cost and may carry a risk of breaching the sterility. One or more of these sensor surfaces, such as at least two, three or four sensor surfaces, may be enzymatic sensor surfaces, i.e. sensors surfaces comprising an immobilized enzyme, although one or more of the sensor surfaces may additionally or alternatively be electrochemical sensor surfaces or sensor surfaces based on optical dyes. Enzymatic sensors are commonly used for e.g. sensing of glucose (using immobilized glucose oxidase) and glutamine (typically using immobilized glutaminase) and may also be used for sensing of other nutrients/metabolites in cell cultivation. Enzymatic sensors need to be refrigerated during storage and may not be compatible with radiation sterilization methods commonly used for bioreactor bags. Hence, there is a particular need for separately packaged enzymatic sensors to be aseptically connected with the bag immediately before use. A first connector unit with enzymatic sensors may e.g. be sterilized using ethylene oxide, hydrogen peroxide or other chemical sterilants. By selecting suitable sensors from the group above and combining them with heat resistant polymers the sensor patch can also be sterilized by autoclaving or electron beam processing. The stability of enzymatic and dye based sensors during sterilization and storage can be enhanced if they are packaged in protective atmosphere (e.g. $N_2$ or Ar) to prevent oxidation. Such a protective atmosphere is easier to achieve for a separate sensor patch than for the whole bag.

In some embodiments, a ratio between a depth 16 and a width 17 of the recess 4 is less than 1, such as less than 0.5 or less than 0.25. It is advantageous to have a low depth-to-width ratio, as this diminishes the risk of clogging the recess with cells during cultivation. The risk for cell clogging can be further reduced by having the sensor surfaces mounted on a movable member, as illustrated in FIG. 3. The movable member can e.g. be an elastic film 18 or a bellows, which after connection can be moved towards the bag interior e.g. by the action of a plunger 19 or by pneumatic action. The sensor surfaces 3 can then be moved to be essentially flush with the bag wall 20 or even to protrude from the bag wall into the interior 29 of the bag 30. Alternatively, the sensor surfaces can be mounted on a fixed member, as illustrated in FIGS. 1 and 2. This provides a simpler design, without moving parts, and facilitates the construction of a connection with low height. A fixed member can e.g. be used with a second connection unit having beveled edges, as discussed below.

In a second aspect, illustrated by FIGS. 1-3, the invention discloses a second connection unit 2, adapted to mate aseptically with the first connection unit 1 as disclosed above. The second connection unit can be mounted, e.g. welded, as a port on the bag wall 20 and may comprise a second terminal surface 13 with an opening 15 in fluid communication with the interior of the bag. The opening may be sealed by a second releasably adherent film 14, such that the contact between the film and the second connection unit and/or the opening 15 is aseptic. The film can e.g. be held in place by an adhesive foam donut 24, applied on the terminal surface 13 of the unit outside the opening 15. The film can also suitably be folded over 180 degrees and, if desired, fitted with a tab 25 to facilitate removal. Further, the second unit may have a gasket 12 mounted on the second terminal surface, adapted to be in sealing abutment with a similar gasket 11 mounted on the first terminal surface 6 of the first connection unit 1. The second releasably adherent film 14 can be arranged to mate with the first releasably adherent film 8 arranged on the first terminal surface 6 of the first connection unit, having a first opening 7, and the first and second films can be adapted to be pulled out together two and two after mating, such that corresponding first 7 and second 15 openings in the first and second terminal end surfaces are mated aseptically.

In some embodiments, a ratio between a depth 26 and a width 27 of the second opening 15 is less than 1, such as less than 0.5 or less than 0.25. It is advantageous to have a low depth-to-width ratio, as this diminishes the risk of clogging the recess with cells during cultivation. Alternatively, or additionally, the second opening can have beveled edges 31 as illustrated in FIG. 2. The bevel can e.g. be such that the second opening 15 has a generally frustoconical shape, with the base 28 of the frustocone oriented towards an inside volume 29 of the bioreactor bag 30. The diameter ratio of the base 28 to the top 35 of the frustocone (or to the width 17 of the first opening in a first connector) may be at least 2.

Figure 4:
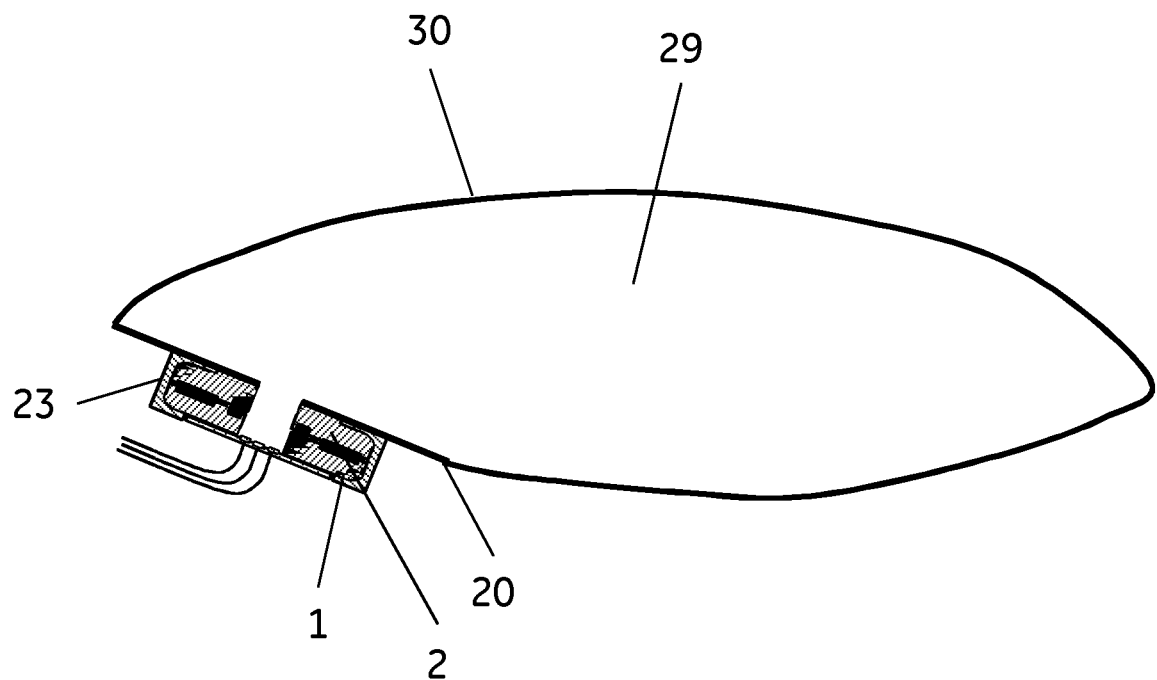
FIG. 4 shows a bioreactor bag with connected and clamped first and second connection units of the invention.

In a third aspect the present invention discloses an aseptic connection formed by the mating of the first connection unit 1 of any one of the embodiments disclosed above with the second connection unit 2 of any one of the embodiments disclosed above. The connection may further comprise a clamp 23, holding the first and second units together. As discussed above, this can e.g. be a Tri-Clamp or Tri-Clover clamp. The clamp may engage the flanges 21,22 of the first and second units. The aseptic connection may have a total height, h, of less than 3 cm, such as less than 2 cm. This enables use of the connection on the bottom side of a rocking bioreactor bag, as in FIG. 4. Placing sensors on the bottom side is preferred, as the bag will only be partially filled with liquid and the sensor must be at least intermittently in contact with the cell culture.

In a fourth aspect, the invention discloses a method of forming an aseptic connection, comprising the steps of:

a) providing a first connection unit as disclosed above and a second connection unit as disclosed above;

b) mating the first unit with the second unit, such that the first and second openings are aligned with each other and the first and second films are in contact with each other, and c) pulling out the first and second films together two and two, such that corresponding first and second openings in the first and second terminal end surfaces are mated aseptically.

In some embodiments, the method further comprises a step d) of applying a clamp over the mated first and second connection units to secure the connection.

In certain embodiments, the second connection unit 2 is arranged on a flexible bioreactor bag 30, with the second opening 15 forming a port in a wall 20 of the flexible bioreactor bag and the method further comprises a step e) of adding cell culture media and cells to the bag.

In some embodiments, the method further comprises a step f) of cultivating cells in the bag and monitoring at least two parameters with the sensor surfaces.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if they were individually incorporated.

The invention claimed is:

1. A first connection unit adapted to mate aseptically with a second connection unit, wherein said first connection unit comprises:

a plurality of sensor surfaces;

a first terminal end surface provided with a first opening of a recess, wherein a ratio between a depth and a width of said recess is less than 1, wherein said first opening is sealed by at least a first releasably adherent film held in place by an adhesive donut on said first terminal end surface outside said first opening, arranged on said first connection unit, so that the contact between the film and the first connection unit is aseptic, and wherein the first connection unit further comprises a movable and deformable member having the plurality of sensor surfaces mounted thereon inside the recess movable and deformable between a pre-mating position within the recess to a mating position essentially flush with the opening of the recess; and a first gasket mounted on said first terminal end surface.

2. The first connection unit of claim 1, wherein said at least a first releasably adherent film is arranged to mate with a second releasably adherent film arranged on a second terminal surface of said second connection unit, having a second opening and a second gasket, and said first and second films are adapted to be pulled out together two and two after mating, such that corresponding first and second openings in said first and second terminal end surfaces are mated aseptically and said first and second gaskets are in sealing abutment with each other.

3. The first connection unit of claim 1, comprising at least one enzymatic sensor surfaces.

4. The first connection unit of claim 1, wherein the movable and deformable member is deformed by action of a plunger or by pneumatic action.

5. The first connection unit of claim 1, comprising at least three sensor surfaces.

6. The first connection unit of claim 1, comprising at least four sensor surfaces.

7. The first connection unit of claim 1, comprising at least two enzymatic sensor surfaces.

8. The first connection unit of claim 1, comprising at least three enzymatic sensor surfaces.

9. The first connection unit of claim 1, wherein the ratio of between a depth and a width of said recess is less than 0.5.

10. The first connection unit of claim 1, wherein the ratio of between a depth and a width of said recess is less than 0.25.

11. The first connection unit of claim 1, wherein the first releasably adherent film is folded over itself 180 degrees and comprises a tab on an edge thereof to facilitate removal.

12. The first connection unit of claim 1, wherein the movable and deformable member is an elastic film.

13. The first connection unit of claim 1, wherein the movable and deformable member is a bellows.

14. An aseptic connection formed by the mating of the first connection unit of claim 1 with a second connection unit adapted to mate specifically with the first connection unit.

15. The aseptic connection of claim 14, having a height of less than 3 cm.

16. A method of forming an aseptic connection, comprising the steps of:
a) providing a first connection unit according to claim 1 and the second connection unit adapted to mate specifically with the first connection unit having a second releasably adherent film arranged on a second terminal surface with a second opening, wherein after mating with said first connection unit having a first releasably adherent film, said first and second films are adapted to be pulled out together two and two after mating, such that corresponding first and second openings in said first and second terminal end surfaces are mated aseptically;
b) mating said first unit with said second unit, such that said first and second openings are aligned with each other and said first and second films are in contact with each other, and
c) pulling out said first and second films together two and two, such that corresponding first and second openings in said first and second terminal end surfaces are mated aseptically.

17. The method of claim 16, further comprising a step d) of applying a clamp over said first and second connection units to secure the connection.

18. The method of claim 16, wherein said second connection unit is arranged on a flexible bioreactor bag, with said second opening forming a port in a wall of said flexible bioreactor bag and wherein said method further comprises a step e) of adding cell culture media and cells to said bag.

19. The method of claim 18, further comprising a step f) of cultivating cells in said bag and monitoring at least two parameters with said sensor surfaces.

* * * * *